United States Patent [19]

Matsumura

[11] Patent Number: 5,078,885
[45] Date of Patent: Jan. 7, 1992

[54] METHOD AND APPARATUS FOR REMOVING PROTEIN-BOUND MOLECULES FROM BODY FLUIDS

[76] Inventor: Kenneth N. Matsumura, 2107 Dwight Way, Berkely, Calif. 94704-2062

[21] Appl. No.: 274,028

[22] Filed: Nov. 21, 1988

Related U.S. Application Data

[63] Continuation-in-part of Ser. No. 499,877, Jun. 1, 1983, abandoned, which is a continuation-in-part of Ser. No. 209,282, Nov. 18, 1980, abandoned, which is a continuation of Ser. No. 40,892, May 21, 1979, abandoned.

[51] Int. Cl.$^5$ ............................................. B01D 61/26
[52] U.S. Cl. ................................. 210/632; 210/638; 210/321.72
[58] Field of Search .................. 210/632, 500.38, 638, 210/321.72

[56] References Cited

U.S. PATENT DOCUMENTS

| | | | |
|---|---|---|---|
| 3,734,851 | 5/1973 | Matsumura | 210/632 |
| 4,056,467 | 11/1977 | Christen et al. | 210/632 X |
| 4,375,414 | 3/1983 | Strahilevitz | 210/638 |
| 4,774,039 | 9/1988 | Wrasidlo | 210/500.38 X |

Primary Examiner—Frank Spear

[57] ABSTRACT

The method for removing molecules bound to proteins in body fluid comprising positioning said body fluid in contact with one side of an albumin-dimensioned bottleneck pore membrane and positioning proximate the opposite side of said membrane aqueously suspended adsorbent. The apparatus comprises an albumin-dimensioned bottle-neck pore membrane and means associated therewith for positioning body fluid to be treated in contact with one side of said membrane and aqueously suspended adsorbent located proximate the opposite side of said membrane.

15 Claims, 5 Drawing Sheets

A = ALBUMIN
\* = BILIRUBIN
DA = DESIGNER ADSORBENT

TO INTERIOR OF MEMBRANE

TO INTERIOR OF MEMBRANE

A = ALBUMIN
* = BILIRUBIN
DA = DESIGNER ADSORBENT

TO INTERIOR OF MEMBRANE

METHOD AND APPARATUS FOR REMOVING PROTEIN-BOUND MOLECULES FROM BODY FLUIDS

FIELD OF THE INVENTION

This application is a continuation-in-part of U.S. application Ser. No. 499,877 filed June 1, 1983, which is a continuation-in-part of 209,282 filed Nov. 18, 1980, which is a continuation of Ser. No. 040,892 filed May 21, 1979 all three previous continuation-in-part applications having been now abandoned.

This invention is in the field of treatment of body fluids and more specifically deals with an improved method for the removal of protein-bound molecules from body fluids.

BACKGROUND OF THE INVENTION

Standard hemodialysis readily removes molecules (e.g., urea, raffinose, and potassium) in the body fluids which are free and not bound to other molecules like proteins. However, molecules such as jaundice-causing bilirubin and tranquilizer diazepam can not be removed from body fluids by standard hemodialysis because such molecules, though small, are bound to larger molecules like albumin (MW 69,000) and other proteins present in the body fluids: standard hemodialysis membranes are not permeable to albumin or large proteins because their pores are too tiny to admit them (FIG. 1); consequently, molecules bound to large proteins remain stuck to the proteins and do not cross the membrane.

SUMMARY OF THE INVENTION

I have developed a novel method for removing from body fluids molecules which are protein-bound. The method is a great boon to the practice of the bio-artificial liver/body fluid purifier that I developed (U.S. Pat. No. 3,734,851) and for the removal of toxic levels of many drugs from body fluids. Other objects and benefits of my invention will become evident in the course of the description which follows.

Generally, in the method comprising positioning body fluid to be treated into contact with one side of a semi-permeable membrane and positioning adsorbent proximate the other side of said membrane, my new invention is the improvement for removing molecules which are bound to proteins in body fluid comprising positioning said body fluid in contact with one side of an albumin-dimensioned bottle-neck pore membrane and positioning proximate the opposite side of said membrane aqueously suspended adsorbent. A further improvement comprises providing means for minute, rapid, to-and-fro partial movement of adsorbents and body fluid proteins into and out of narrow end of the pores of said membrane. In the apparatus comprising a semi-permeable membrane, means associated therewith for positioning body fluid to be treated in contact with one side of said membrane and adsorbents located proximate the opposite side of said membrane, the apparatus of my invention is the improvement comprising an albumin-dimensioned bottle-neck pore membrane and means associated therewith for positioning body fluid to be treated in contact with one side of said membrane and aqueously suspended adsorbent located proximate the opposite side of said membrane.

DETAILED DESCRIPTION OF THE INVENTION

Figure 1:
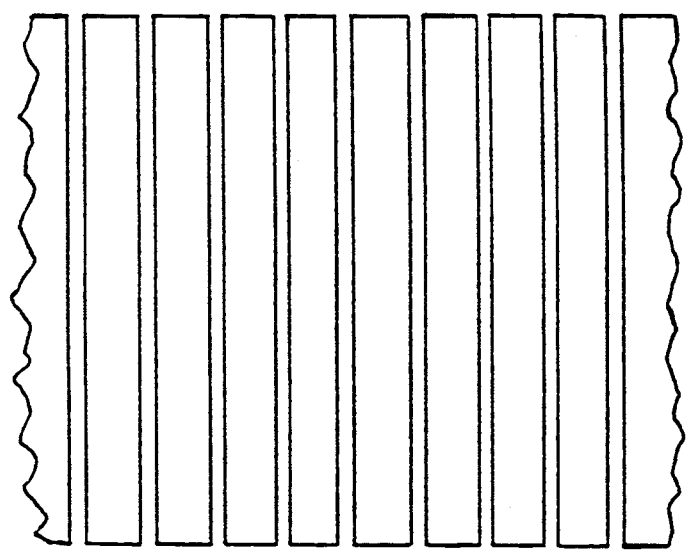
FIG. 1 is a cross-section of a standard hemodialysis membrane. Note the uniform diameter of the pore throughout its length. It is not possible to remove protein bound molecules from body fluids using this type of membrane.
Figure 2A:
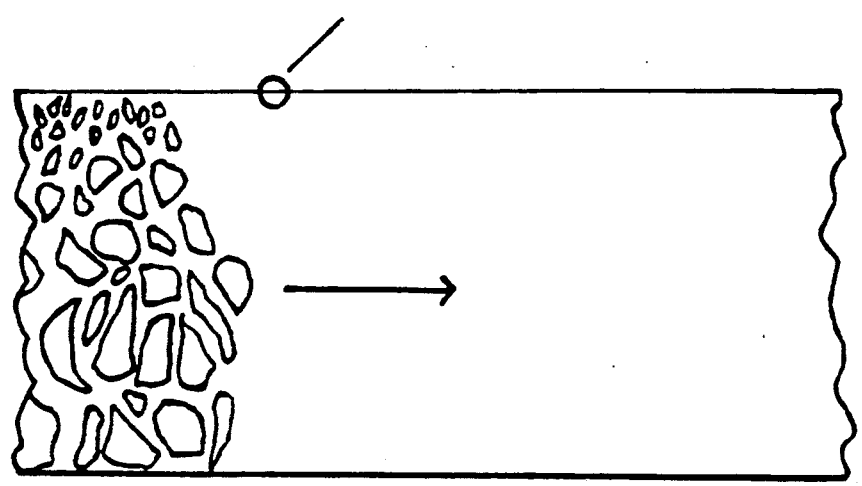
FIG. 2a is a cross-section of the novel bottle-neck pore membrane which, together with adsorbents, allows the removal of molecules which are bound to proteins in the body fluid. The removal is accomplished without the loss of vital body fluid proteins like albumin.
Figure 2B:
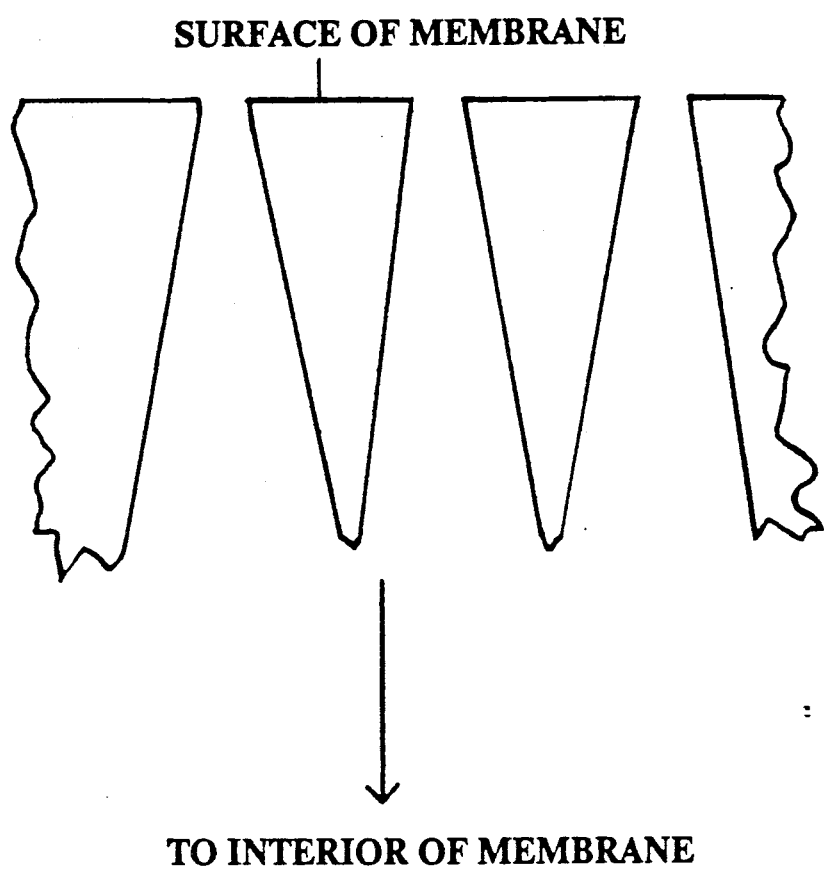
FIG. 2b is a blown up image of the cross-section at center of the circle in FIG. 2a. The pore size becomes smaller and smaller towards the surface on this side of the membrane. However, the requirement at the bottle-neck end of the pores is a functional one. The vertical dimension at the bottle neck is the minimum necessary relative to the pore size to block the complete cross over of the albumin molecule to the other side of the membrane. Beyond the bottle-neck, the pore widens immediately as it courses into the interior of the membrane.
Figure 3:
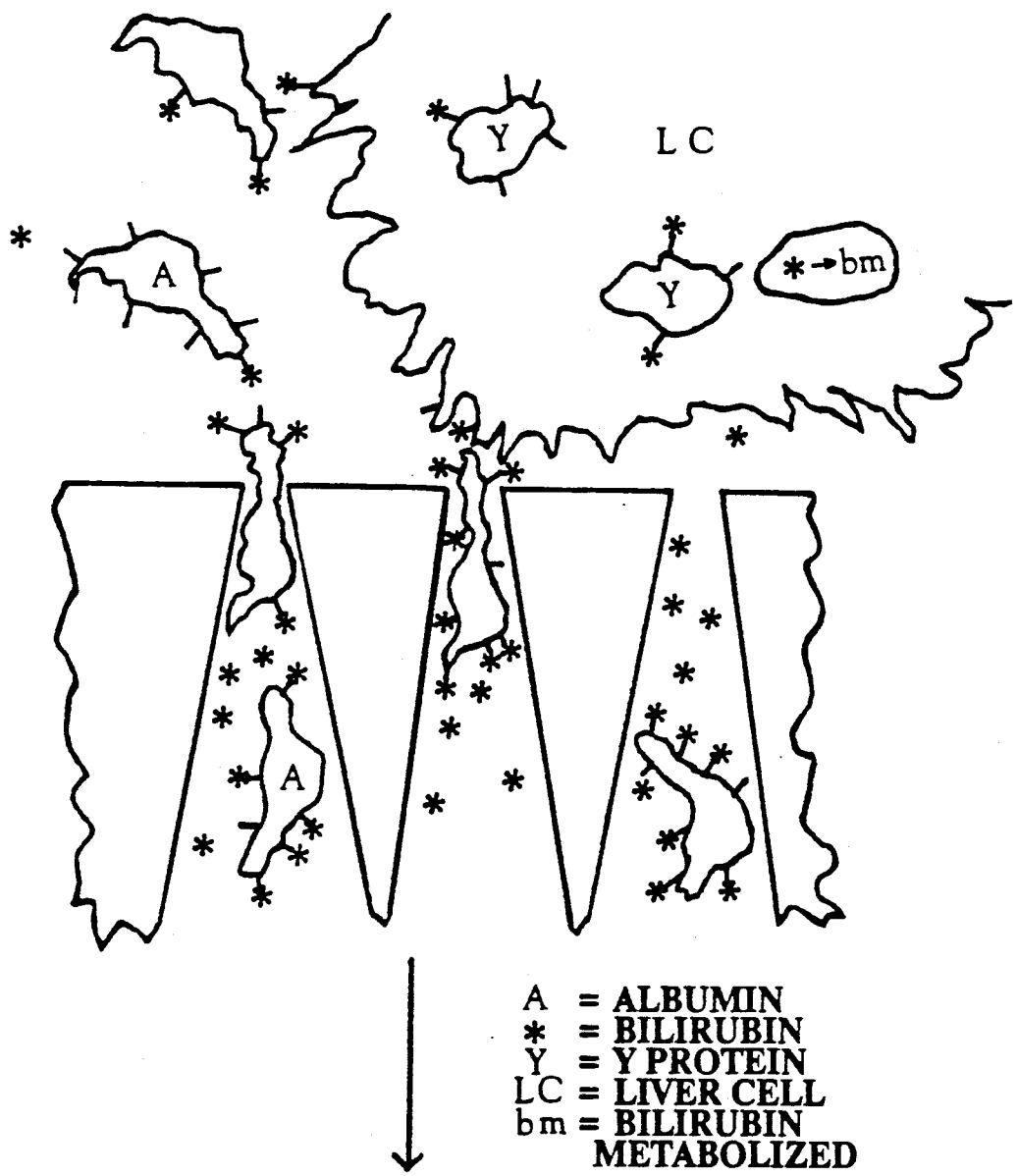
FIG. 3 shows that the narrow bottle-neck end of the pores prevents body fluid proteins like albumin from completely crossing the membrane; in a preferred embodiment, however, the bottle-neck is so dimensioned that a substantial portion of the protein molecule can cross the narrow end and extend itself out of the bottle-neck area to the other side of the membrane. While "waving" its arm on the other side of the membrane, the body fluid proteins can contact adsorbents on the other side. During this contact, adsorbents can "grab" away molecules like bilirubin which are loosely bound to the body fluid proteins. When this type of direct contact is possible between the adsorbent and the albumin, transfer kinetics of the bound molecules is maximal. However, short of achieving direct contacts, bringing the albumin molecule and the adsorbent as close as possible considerably enhances the transfer of the bound molecules across the membrane.
Figure 4:
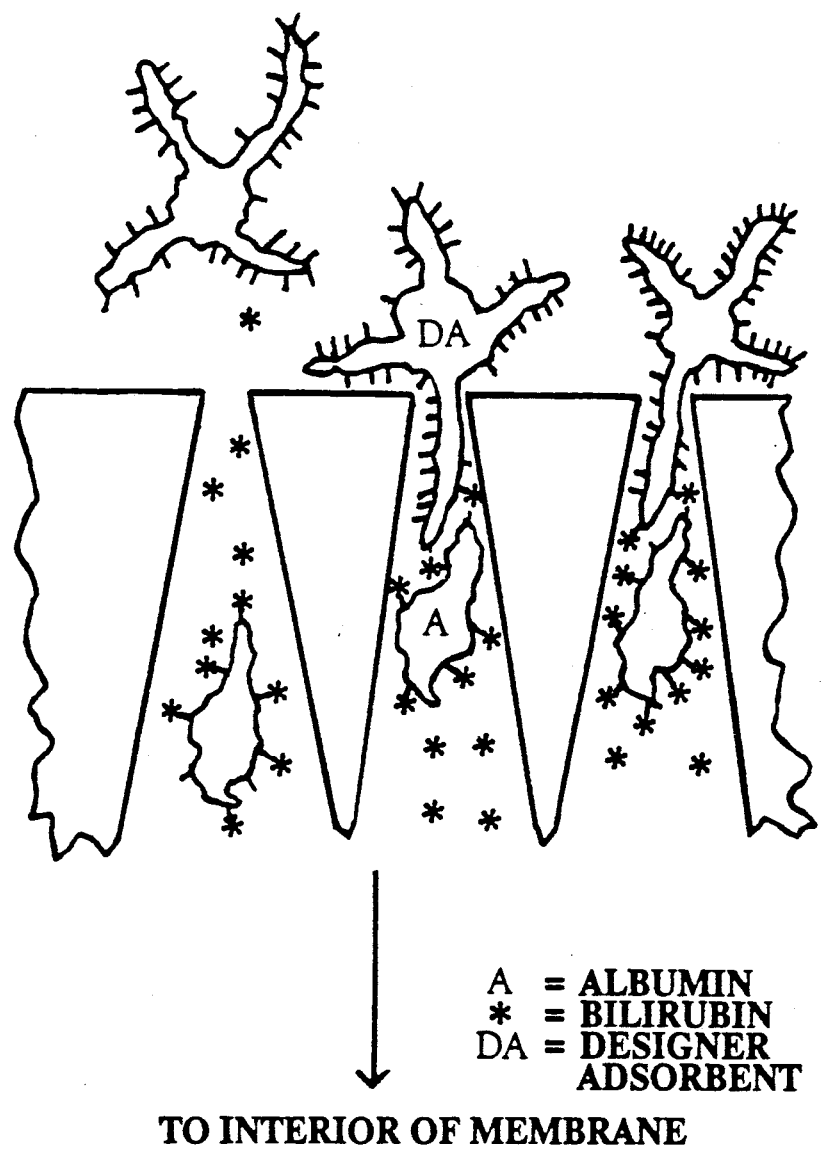
FIG. 4 shows that the narrow bottle-neck end of the pores prevents adsorbents from completely crossing the narrow end of the pores. However, in a preferred embodiment, the bottle-neck and the adsorbent are so dimensioned that a substantial portion (i.e., the binding arm) of the adsorbent can cross the bottle-neck and into the depth of the pores. In the depth of the pores, the adsorbents contact body fluid proteins from the other side of the membrane and "grab" away molecules such as bilirubin which are loosely bound to body fluid proteins.

By albumin-dimensioned bottle-neck pore membrane, I mean a membrane like that shown in FIGS. 2a and 2b. It can be various materials, including cellulose acetate. Given the specification contained herein, one can obtain a suitable membrane from custom membrane fabricators who will use controlled solvent-evaporation and drying methodology* (see K. K. Sirkar et al. The effect of short air exposure period on the performance of cellulose acetate membranes from casting solutions with high cellulose acetate content. J. Applied Polymer Sci. 1978; 22: 1919–1944 for principles and references) to fabricate a membrane that meets the specification described herein. The narrow end of the pore serves as a bottle-neck to prevent larger molecules like albumin and proteins (MW>50,000) from passing through the pore completely; however, the bottle-neck is the minimum necessary to prevent albumin cross-over and the pore beyond the bottle-neck widens as it courses into the interior of the membrane as shown in FIG. 2b. Therefore, the bottle-neck is said to be dimensioned by the size, geometry and chemistry of the albumin molecule. Since the pore is narrow only at its bottle-neck, in a preferred embodiment the other parts of the pores are large enough to admit albumin molecules. So admitted albumin molecules can come close to the other side of the membrane, even partially crossing the bottle-neck (FIG. 3). Albumin molecules that come close enough to the other side can contact some adsorbent molecules that reach partially into the pore interior (FIG. 4). In a standard dialysis test cell, albumin-dimensioned bottle-neck pore membrane, of course, tests substantially negative for leakage (cross-over) of larger proteins like serum albumin.

\* Basically, in the standard membrane casting procedure of Loeb-Sourirajan and Manjikian (references cited by Sirkar article), permeability characteristics of the asymmetric cellulose acetate membrane are governed by the ultra-thin (often under 0.5 microns) skin that one forms on a thicker (typically 8 to 30 microns), large-porous layer. Like the skin that forms on the surface of a hot cup of chocholate milk, the skin of the cellulose acetate membrane forms when a mixture of cellulose acetate with solvents like acetone and formamide is exposed to air. At the air-solvent interphase, the volatile solvent (acetone) evaporates into air leaving a denser concentration of cellulose acetate right at the air-solvent interphase. The pore and thickness characteristic of the skin is governed by how one accomplishes this evaporation. The amount and the rate of evaporation is controllable by such factors as adjusting the environmental temperature (slower evaporation at lower temperature), varying the duration of evaporation, by varying the partial pressure of the evaporating solvent in air, and by using solvents of different volatility (for example, dioxane has a higher boiling temperature). One can obtain a very thin skin by using a short air exposure time. In this case, one gets a sharply demarcated margin in which very large pores are suddenly adjacent to tiny pores of the skin. To obtain a more gradual transition in the pore dimension, especially within the skin layer, one evaporates slowly over a longer time.

The definition and requirements of albumin-dimensioned bottle-neck pore membrane is functional rather than based on any specific geometry of the pores of the membrane. Different geometric and chemical characteristics at the bottle neck can provide the functional requirements that albumin not be able to completely cross the membrane but that pore dimension elsewhere be large enough so that large molecules like albumin on either side of the membrane are able to come as close as possible to each other, even colliding with each other across the bottle neck to maximize the transfer kinetics of the molecules which are bound to albumin. Other requirements that is fulfilled by this membrane are rather obvious. The membrane is tear resistant for the purpose. Typically, the membrane is about 8 micron thick.

While I believe I am the first to call for the albumin-dimensioned bottle-neck pore membrane, the emphasis in my invention is not to the membrane per se but to the unforeseen new use for this membrane. Since albumin-dimensioned bottle-neck pore membranes can sometimes be no more permeable than standard hemodialysis membrane to unbound solutes, other have failed to see that albumin-dimensioned bottle-neck pore membrane can be so different in removing those solutes when they are bound to albumin in body fluids. When trying to remove molecules that are bound to albumin by using adsorbents across standard hemodialysis membranes, people observed that decreasing the thickness of the membrane even by 66% made no measurable difference. Therefore, it appeared to other the removal of bound molecules did not follow the standard principle that expects better permeability of membrane merely by decreasing its thickness. One commonly finds a statement in journals that a substance is plasma protein-bound and so not dialyzable. I know of otherwise skillful scientists who have wasted many years by not realizing that a different principle applies here and who chose other standard membranes for the task believing no difference existed. I myself stumbled upon the new principle quite by accident when by chance I chose to work with an asymmetric cellulose acetate membrane. While standard asymmetric cellulose acetate membranes used in dialysis are a far cry from albumin-dimensioned bottle-neck pore membrane, I noticed that they worked better than homogeneous hemodialysis membrane like those of regenerated cellulose or polyacrilonitrile in removing molecules that are albumin-bound. I began to explore the reasons and through these reasonings I developed the basis for my invention. I must indeed emphasize that it was entirely unexpected that asymmetric cellulose acetate membranes worked better than polyacrilonitrile membrane because the latter membrane has a better permeability characteristics for free solutes. Yet, I was able to remove zero amounts of bilirubin from serum using polyacrilonitrile membrane with liver cells, while I was able to remove significant amounts of bilirubin using an asymmetric cellulose acetate membrane. Bilirubin, of course, exists in serum almost completely bound to albumin.

Regarding other components of my invention, by the term adsorbents, I means such molecules like albumin which bind the molecules to be removed from the body fluid (these are referred to as molecular adsorbents). I also means tissue homogenates (e.g., liver) which contain a mixture of natural binder molecules like "y" protein in the liver cells which competetively binds bilirubin off of plasma albumin. The adsorbents must be by geometry (size and shape) and chemistry (electrical charge relative to the electrical charge of the wall of the pores) incapable of completely crossing the narrow end of the pores. However, ideally, a substantial portion of the adsorbent molecule could cross the narrow end of the pores and into the depth of the pores (FIG. 4).

By the term adsorbents, I do not limit my definition to a single molecule or a polymer, but I also mean intact cells and cellular fragments or components. Liver cells are functionally active in binding molecules like bilirubin and drugs. The advantage that a cell possesses which a simple molecule does not, is that the cell's binding capacity does not saturate so easily, because typically the cell will also metabolize and/or breakdown molecules it binds so that its binding capacity is renewed in the process. Other cells than liver cells have binding receptors for certain molecules and therefore are useful in removal of such molecules. Unlike simple molecules, cells are also "smart", by which I mean that cells are capable of being more selective in removing harmful molecules over vital ones.

By the term adsorbent, I do not exclude the use of a mixture of adsorbents. In a preferred embodiment of my invention, both a molecular adsorbent, like albumin, and liver cells are used.

Adsorbents must be of size and shape such that they can not completely cross the membrane. In a preferred embodiment, the adsorbent molecule comprises an extensive binding arm able to cross over the narrow end of the pore and an impedence body incapable of crossing said narrow end. The strength with which absorbent molecule binds molecules to be removed from body fluids should be comparable to the strength with which albumin binds the molecules to be removed when said adsorbent molecule is to be used together with cell adsorbent. When used alone, such adsorbent molecule may bind molecules more effectively than albumin. Both geometry and chemistry govern the ability of binder arm to cross the narrow end of the pore. Likewise, both geometry and chemistry govern the inability of the impedence body to cross the narrow bottle neck. When such an adsorbent molecule is chemically fabricated, it can be called, "designer adsorbent."

Adsorbents may be commercially purchased. Liver cells can be obtained by the methods of Seglen (Seglen, P.O. Preparation of rat liver cells. Exp. Cell Res. 1974; 74:450-4).

By the term aqueous suspension, I mean that adsorbents are dissolved in or suspended in aqueous fluid, like physiologic salt solution.

My invention may be practiced with body fluid on the narrow pore side of the membrane or on the opposite side, but in a preferred embodiment, the body fluid is on the opposite side.

In a preferred embodiment, means are provided to cause adsorbents and body fluid proteins on both sides of the membrane to move to-and-fro partially into and out of the membrane pores. The large molecules, of course, do not completely cross the membrane but parts of the molecules may cross the membrane pore's narrow end. For example, the apparatus of my invention can be placed on a vibrating platform, which allows for rapid to-and-fro movements of suspended molecules. Another example is to cause fluids on either or both sides of the membrane to be made to flow across the surface of the membrane by a peristaltic pump which creates minute, rapid pulsatile flow. While peristaltic pumps are used routinely in hemodialysis application, in this preferred embodiment, I mean to use a modification of such a pump to deliver substantially more pulsations per minute than in standard hemodialysis. This goal can be achieved by adding more rollers to the pump or by decreasing the lumen size of the tubing being squeezed by the rollers and then operating the pump at a higher speed than standard.

In another preferred embodiment, the fluid suspending an adsorbent in contact with the body fluid being treated across the membrane is removed from contact with the membrane, chemically treated to remove bound molecules removed from the body fluid, and returned into contact with the membrane. In this manner, the body fluid is continuously treated by readily binding adsorbents. It will be understood that the drawings and specific description have been given for purposes of illustration only and that variations and modifications can be made therein without departing from the spirit and scope of the appended claims.

Having described my invention, I claim:

1. In the method comprising positioning body fluid to be treated into contact with one side of a semi-permeable membrane and positioning adsorbent proximate the other side of said membrane, the improvement comprising removing molecules which are bound to proteins in body fluid by positioning said body fluid in contact with one side of an albumin-dimensioned bottle-neck pore membrane and positioning proximate the opposite side of the said membrane aqueously suspended adsorbent.

2. The invention of claim 1 wherein means are provided to cause to-and-fro movements of adsorbents and body fluid proteins partially into and out of the narrow end of pores of said membrane.

3. The invention of claim 1 wherein adsorbents are placed on the side of said membrane having the narrow bottle-neck end of the pores and the body fluid is placed on the opposite side of said membrane.

4. The invention of claim 1 wherein the aqueous fluid suspending said adsorbent is removed from contact with said membrane, said adsorbent is chemically treated to remove bound molecules removed from said body fluid, and the aqueous fluid suspending said adsorbent is returned into contact with said membrane.

5. The invention of claim 1 wherein said adsorbent is liver cells.

6. The invention of claim 1 wherein said adsorbent is molecular adsorbent and liver cells.

7. The invention of claim 1 wherein said adsorbent is liver homogenate.

8. The invention of claim 1 wherein said adsorbent is a designed adsorbent.

9. In the apparatus comprising a semi-permeable membrane, means associated therewith for positioning body fluid to be treated in contact with one side of said membrane and adsorbents located proximate the opposite side of said membrane, the improvement comprising an albumin-dimensioned bottle-neck pore membrane, means for removing molecules which are bound to proteins in said body fluid, means associated with said membrane for positioning body fluid to be treated in contact with one side of said membrane, and aqueously suspended adsorbent located proximate the opposite side of said membrane.

10. The invention of claim 9 wherein means are provided to cause to-and-fro movements of adsorbent and body fluid protein partially into and out of narrow end of pores of said membrane.

11. The invention of claim 9 wherein means are provided for withdrawing said aqueous fluid suspending adsorbent from contact with said membrane, additional means are provided for chemical treatment of said adsorbent to remove bound molecules removed from said body fluid, and means are provided to return said treated adsorbent suspended in aqueous fluid into contact with said membrane.

12. The invention of claim 9 wherein said adsorbent is liver cells.

13. The invention of claim 9 wherein said adsorbent is molecular adsorbent and liver cells.

14. The invention of claim 9 wherein said means for positioning adsorbent in contact with said membrane is on the side of the membrane having narrow bottle-neck end of pores and said means for positioning body fluid in contact with said membrane is on the opposite side of said membrane.

15. The invention of claim 9 wherein adsorbent is designer adsorbent.

* * * * *